(12) United States Patent
Schussler, III

(10) Patent No.: US 6,174,834 B1
(45) Date of Patent: Jan. 16, 2001

(54) OXYCHLORINATION CATALYST

(75) Inventor: Henry W. Schussler, III, Harrison City, PA (US)

(73) Assignee: PPG Industries Ohio, Inc., Cleveland, OH (US)

(*) Notice: Under 35 U.S.C. 154(b), the term of this patent shall be extended for 0 days.

(21) Appl. No.: 09/286,064

(22) Filed: Apr. 5, 1999

(51) Int. Cl.[7] .................. B01J 27/122; B01J 29/04; B01J 23/02; B01J 29/87; B01J 23/70

(52) U.S. Cl. .................. 502/225; 502/60; 502/80; 502/84; 502/87; 502/243; 502/244; 502/344; 502/345

(58) Field of Search .................. 502/225, 243, 502/244, 60, 80, 84, 87, 345, 344

(56) References Cited

U.S. PATENT DOCUMENTS

| | | | |
|---|---|---|---|
| 2,951,103 | 8/1960 | Ellsworth et al. | 260/654 |
| 3,256,352 | 6/1966 | Bohl et al. | 260/654 |
| 3,288,868 | 11/1966 | Piester | 260/654 |
| 3,296,319 | 1/1967 | Bohl et al. | 260/654 |
| 3,345,422 | 10/1967 | Piester et al. | 260/650 |
| 3,378,597 | 4/1968 | Dehn et al. | 260/652 |
| 3,461,084 * | 8/1969 | Li | 502/225 |
| 3,679,373 | 7/1972 | Vancamp et al. | 23/288 L |
| 3,691,098 * | 9/1972 | Calcagno et al. | 502/225 |
| 3,699,176 * | 10/1972 | Suzuki et al. | 570/245 |
| 4,151,212 | 4/1979 | Rideout | 260/659 A |
| 4,172,052 | 10/1979 | Foster | 252/442 |
| 4,377,491 * | 3/1983 | Canavesi et al. | 502/225 |
| 4,414,136 * | 11/1983 | Convers | 502/225 |
| 4,446,249 * | 5/1984 | Eden | 502/225 |
| 4,451,683 * | 5/1984 | Davies et al. | 570/224 |
| 4,460,699 * | 7/1984 | Convers et al. | 502/84 |
| 4,740,642 * | 4/1988 | Eden et al. | 570/243 |
| 4,740,644 * | 4/1988 | Eichhorn et al. | 570/245 |
| 4,849,393 * | 7/1989 | Eden et al. | 502/225 |
| 5,004,849 * | 4/1991 | Hirschmann et al. | 570/224 |
| 5,011,808 * | 4/1991 | Scott | 502/225 |
| 5,070,062 * | 12/1991 | Canavesi et al. | 502/225 |
| 5,098,878 * | 3/1992 | Hirschmann et al. | 502/225 |
| 5,116,799 * | 5/1992 | Correia et al. | 502/225 |
| 5,227,548 * | 7/1993 | Scott | 570/243 |
| 5,231,156 | 7/1993 | Lin | 526/279 |
| 5,260,247 * | 11/1993 | Helmut et al. | 502/225 |
| 5,354,789 | 10/1994 | Komatsu et al. | 570/203 |
| 5,382,726 * | 1/1995 | Young et al. | 502/341 |
| 5,527,754 * | 6/1996 | Derleth et al. | 502/225 |

FOREIGN PATENT DOCUMENTS

| | | |
|---|---|---|
| 1 412 336 | 5/1975 | (GB) . |
| 159843 | 3/1988 | (PL) . |

\* cited by examiner

*Primary Examiner*—Mark L. Bell
*Assistant Examiner*—Patricia L. Hailey
(74) *Attorney, Agent, or Firm*—George D. Morris; William C. Mitchell

(57) ABSTRACT

Oxychlorination catalyst is produced by mixing together wet support material, copper chloride or precursor thereof, to form a paste, wherein the wet support material is wet clay, wet silica, wet silica gel, wet alumina, wet diatomaceous earth, or a mixture of two or more thereof; removing water from the paste to produce a substantially dry mixture; and calcining the substantially dry mixture at elevated temperatures to produce a calcined mixture wherein alkali metal chloride or precursor thereof is mixed with the wet support material or an aqueous solution of alkali metal chloride or precursor thereof is applied to the paste, the substantially dry mixture, or the calcined mixture and the water of the aqueous solution is substantially removed. Preferably wet attapulgus clay, cupric chloride, and potassium chloride are mixed to form the paste.

32 Claims, No Drawings

OXYCHLORINATION CATALYST

BACKGROUND OF THE INVENTION

Oxyhydrochlorination processes wherein ethylene, hydrogen chloride, and molecular oxygen are reacted in the presence of oxychlorination catalyst to form 1,2-dichloroethane [CAS 107-06-2], are themselves well known; see U.S. Pat. Nos. 3,256,352; 3,288,868; 3,345,422; 3,378,597; 3,679,373; 4,151,212; and 4,172,052. The process is usually conducted either in a fluidized bed of oxychlorination catalyst particles at elevated temperatures in the range of from 190° C. to 350° C., or in a fixed bed of oxychlorination catalyst particles at elevated temperatures in the range of from 200° C. to 450° C. When ethylene is so oxyhydrochlorinated, satisfactorily high yields of 1,2-dichloroethane may be obtained under moderate reaction conditions. However, the product typically contains objectionable amounts of chloral, i.e., amounts in excess of about 0.2 percent by weight. In addition to being classified as a pollutant, the normal boiling point of chloral is quite close to that of 1,2-dichloroethane. Chloral is therefore both difficult and costly to remove by distillation to produce high purity 1,2-dichloroethane.

Oxychlorination catalysts have been manufactured in the past by milling attapulgus clay with water, extruding the milled clay into pellets, drying the pellets, calcining the dried pellets, grinding the dried pellets and screening to form particles of appropriate size, adding a hot aqueous solution of cupric chloride and potassium chloride to the particles, and drying to remove water and thereby form substantially dry catalyst particles. The addition of the hot aqueous solution of cupric chloride and potassium chloride to the particles is usually accomplished either by spraying the hot solution onto heated clay particles in a tumbling vessel or by spraying the hot solution into a heated fluidized bed of the particles. Rescreening may be performed to verify the correct particle size distribution.

Oxychlorination catalysts have also been made by mixing attapulgus clay, water, an aqueous solution containing cupric chloride and potassium chloride to form a slurry, drying the slurry at 160° C. for 48 hours in a forced draft oven to form a dried cake, breaking up the cake, and grinding the broken cake to −70 to +200 mesh; See, for example, U.S. Pat. No. 4,151,212. See also U.S. Pat. No. 4,172,052 which discloses drying slurries at 105° C. and grinding the resulting cakes.

SUMMARY OF THE INVENTION

A new process has now been found which produces a new oxychlorination catalyst having improved catalytic characteristics. The new catalyst when used for the oxyhydrochlorination of ethylene to form 1,2-dichloroethane has been observed to result in markedly reduced chloral formation as compared to prior catalyst where both the cupric chloride and potassium chloride were sprayed onto preformed pellets or particles. Depending upon conditions, reductions in chloral formation of from 30% to 75% have been achieved.

Accordingly, a first embodiment of the invention is a process for producing oxychlorination catalyst comprising: (a) mixing together wet support material and copper chloride or precursor thereof to form a paste, wherein the wet support material is wet clay, wet silica, wet silica gel, wet alumina, wet diatomaceous earth, or a mixture of two or more thereof; (b) removing water from the paste to produce a substantially dry mixture; and (c) calcining the substantially dry mixture at elevated temperatures of at least 600° C. to produce a calcined mixture; wherein: (d) alkali metal chloride or a precursor thereof is mixed with the wet support material and copper chloride or precursor thereof, to form the paste; or (e) an aqueous solution of alkali metal chloride or precursor thereof is applied to the paste, the substantially dry mixture, the calcined mixture, or two or more thereof, and the water of the aqueous solution is substantially removed.

A second embodiment of the invention is oxychlorination catalyst produced by the process of the first embodiment.

In an oxyhydrochlorination process wherein ethylene, hydrogen chloride, and molecular oxygen are reacted in the presence of oxychlorination catalyst to form 1,2-dichloroethane, a third embodiment of the invention is the improvement wherein the oxychlorination catalyst has been produced by the process of the first embodiment.

In an oxyhydrochlorination process wherein 1,2-dichloroethane, hydrogen chloride, and molecular oxygen are reacted in the presence of oxychlorination catalyst to form perchloroethylene and trichloroethylene, a fourth embodiment is the improvement wherein the oxychlorination catalyst has been produced by the process of the first embodiment.

DETAILED DESCRIPTION OF THE INVENTION

The support material may be any commonly used catalyst carrier, e.g., silica, silica gel, alumina, diatomaceous earth, and the like. If the catalyst is to be used in a fluidized rather than a fixed bed, silica or high silica or alkali metal silicate content clay minerals are preferred support materials, some examples of which are bentonite, kaolite, illite and attapulgite clay minerals. Alumina or high alumina content clay materials, e.g., diaspore and bauxite clays, may be used; however, these have been found to be somewhat more friable and to have a higher attrition rate when used in a fluidized bed than the predominately silica or alkali metal silicate containing clays. Of the clay minerals, attapulgus clay is particularly preferred.

The initial support material may be wet or dry, but water should be present at some point during mixing with the other materials in order to form a paste. When the support material contains insufficient water, water may be added neat, as a solvent for one or more of the added salts, or both. When the support material contains too much water, water may be removed.

The copper chloride is cupric chloride, cuprous chloride or a mixture thereof. Precursors of copper chloride are those copper compounds or metallic copper which are converted to copper chloride under the oxychlorination conditions prevailing in the oxychlorination reactor in which they are used. The more common precursors of copper chloride include copper bromide, copper iodide, copper oxide, metallic copper, and a mixture of two or more thereof. The copper bromide may be cupric bromide, cuprous bromide, or a mixture thereof. The copper iodide may be cupric iodide, cuprous iodide, or a mixture thereof. The copper oxide may be cupric oxide, cuprous oxide, or a mixture thereof. Hydrates of the various copper compounds may be used where they exist.

The alkali metal chloride may be sodium chloride, potassium chloride, lithium chloride, rubidium chloride, cesium chloride, or a mixture of two or more thereof. Potassium chloride, sodium chloride, or a mixture thereof is generally used. The preferred alkali metal chloride is potassium chloride. Precursors of alkali metal chloride are those alkali metal compounds which are converted to alkali metal chloride under the oxychlorination conditions prevailing in the oxychlorination reactor in which they are used. Exemplary precursors of the alkali metal chlorides include potassium bromide, potassium iodide, sodium bromide, sodium iodide, lithium bromide, lithium iodide, rubidium bromide, rubidium iodide, cesium bromide, cesium iodide, and mixtures of two or more thereof. Hydrates of the various alkali metal compounds may be used where they exist.

The quantity of copper chloride or precursor thereof used in the preparation of the catalyst are such that the copper content of the catalyst is from 4 to 15 percent by weight, preferably from 5 to 12 percent by weight based on the total weight of catalyst, i.e., combined weights of metal halides plus support material.

The quantity of alkali metal chloride or precursor thereof used in the preparation of the catalyst is such that the alkali metal content of the catalyst is from 2 to 12 percent by weight, preferably from 3 to 10 percent by weight based on the total weight of catalyst, i.e., combined weights of metal halides plus support material.

It is to be understood that copper content of the catalyst and alkali metal content of the catalyst refer to that copper content and alkali metal content resulting from treating the support material with the respective compounds, and does not include copper and alkali metal inherently present in the untreated support material.

One or more chlorides of one or more metals other than copper or alkali metal, or one or more precursors thereof, may optionally also be included in the metal compounds mixed with the support material to form the paste. Such compounds, when used, are generally employed in minor amounts compared to the copper and alkali metal compounds.

The wet support material, copper chloride or precursor thereof, and optionally, the alkali metal chloride or precursor thereof, may be combined in any order and mixed to form a paste using any conventional mixing techniques, such as for example, milling.

The water content of the paste may vary widely. Usually, however, the paste comprises from 35 to 75 percent water by weight. In many cases the paste comprises from 40 to 70 percent water by weight. From 50 to 60 percent water by weight is preferred.

Water may be removed from the paste to form the substantially dry mixture by any known procedure such as by heating in an oven at ambient atmospheric or subatmospheric pressure. Usually the paste is heated at temperatures in the range of from 80° C. to 200° C. to produce the substantially dry mixture. Preferably the temperatures are in the range of from 120° C. to 160° C.

The substantially dry mixture is calcined at elevated temperatures of at least 600° C. to form the calcined mixture. Often the temperatures are in the range of from 600° C. to 1000° C. Preferably the temperatures are in the range of from 700° C. to 900° C.

The substantially dry mixture should be exposed to the calcining temperatures for a time sufficient to produce a calcined mixture. Usually the calcining time is at least one hour. In most instances the calcining time is in the range of from 1 hour to 12 hours. Preferably the calcining time is in the range of from 2 hours to 10 hours.

When desired, the calcined mixture may be ground to form particles. Preferably the particles are classified to the desired size.

When the alkali metal chloride or a precursor thereof is not mixed with the wet support material and copper chloride or precursor thereof, to form the paste, then an aqueous solution of alkali metal chloride or precursor thereof is applied to the paste, the substantially dry mixture, the calcined mixture, or two or more thereof, and the water of the aqueous solution is substantially removed. Water may be removed by any known procedure such as by heating. Usually the heating is conducted at temperatures in the range of from 80° C. to 200° C. Preferably the temperatures are in the range of from 120° C. to 160° C. The foregoing procedure may also be used to introduce additional alkali metal chloride or precursor thereof even when some alkali metal chloride or precursor thereof has been mixed with the support material and copper chloride or precursor thereof, to form the paste.

In a typical practice of the invention, ethylene, hydrogen chloride, and oxygen gases are fed in known manner to a reactor at a rate sufficient to maintain the catalyst bed in a fluidized condition without significant entrainment of catalyst particles in the product gas and to intimately contact the gaseous reactants with the fluidized catalyst. Particle size of the catalyst is not particularly critical, although for fluid bed operation, catalyst particle size is typically in the range of from 30 to 200 mesh (U.S. Sieve Series), preferably in the range of from 40 to 100 mesh. The reaction may be conducted over a wide range of temperature, for example, in the range of from 150° C. to 500° C., preferably in the range of from 250° C. to 350° C. Contact time between the gaseous reactants and the catalyst is usually not more than about two minutes and often on the order of about 10 seconds. Depending on reaction conditions, conversion of ethylene to 1,2-dichloroethane usually ranges from about 70 percent to substantially quantitative, and crude 1,2-dichloroethane having a 1,2-dichloroethane content of from 97 percent to 99 percent by weight may be obtained.

Of course the vapor phase oxychlorination of ethylene to 1,2-dichloroethane may be conducted using a fixed catalyst bed rather than a fluidized catalyst bed in the known manner and under known process conditions.

Not only may the oxychlorination catalyst of the invention be used for the vapor phase oxyhydrochlorination of ethylene to 1,2-dichloroethane, but it may be used as the catalyst for many other vapor phase catalytic oxychlorination reactions. Examples include, but are not limited to: the reaction of 1,2-dichloroethane, hydrogen chloride, and molecular oxygen to form perchloroethylene [CAS 127-18-4] and trichloroethylene [CAS 79-01-6]; the reaction of ethylene, hydrogen chloride, and molecular oxygen to form perchloroethylene and trichloroethylene; the reaction of ethylene, molecular chlorine, and molecular oxygen to form 1,2-dichloroethane; the reaction of 1,2-dichloroethane, molecular chlorine, and molecular oxygen to form perchloroethylene and trichloroethylene; the reaction of ethylene, molecular chlorine, and molecular oxygen to form perchloroethylene.

The various oxyhydrochlorination and other oxychlorination reactions may be conducted using a single pass of reactants through the reactor, or a recycle may be employed. Similarly, reactants may be passed through several reactors connected in series, in parallel, or in a combination thereof; recycle may optionally be used when desired.

Other than in the operating examples, or where otherwise indicated, all numbers expressing quantities of ingredients or reaction conditions used herein are to be understood as modified in all instances by the term "about".

The invention is further described in conjunction with the following examples which are to be considered illustrative rather than limiting, and in which all parts are parts by weight and all percentages are percentages by weight unless otherwise specified.

In the Examples which follow, a vertical tube 127 centimeters in height and about 5.3 centimeters in internal diameter (nominal 2-inch Schedule 40 pipe) was employed as a fluidized bed reactor. The reactor was enclosed in a jacket having an internal diameter of about 14.6 centimeters (nominal 6 inch Schedule 80 pipe) which formed an annular heat exchange system. Diphenyl-diphenyl oxide eutectic mixture heat transfer fluid was circulated in the annular space between the jacket and the outer surface of the reactor to heat and cool the fluidized bed as necessary. A reducer at the bottom of the reactor reduced the diameter to about 1.9 centimeters and formed a feed gas inlet through which mixtures of ethylene, hydrogen chloride, oxygen, and nitrogen were introduced to the reactor at rates sufficient to maintain the particulate catalyst in a fluidized condition. A ceramic ball 2.54 centimeters in diameter placed in the reducer prevented catalyst from filling and plugging the feed line to the reactor. A thermowell having a nominal diameter of about 0.95 centimeter was placed concentrically in the reactor. Five thermocouples were located in the thermowell 1.3, 18.0, 33.5, 64.8, and 95.3 centimeters, respectively, above the top of the ceramic ball in its normal resting position. Gaseous effluent was removed from the top of the reactor and condensed. The reactor was controlled using the "hotspot" temperature, which is the highest temperature indicated by any of the five thermocouples.

EXAMPLE 1

A 2-liter Erlenmeyer flask was charged with 827 grams of deionized water. Technical Grade $CuCl_2.2H_2O$ in the amount of 550.6 grams was added to the water with stirring. The solution was heated to 60° C. and then 286.9 grams of potassium chloride was added. The contents of the flask were stirred until all solids were dissolved to thereby produce a stock copper chloride-potassium chloride solution.

Four hundred grams of milled raw attapulgite clay, containing approximately 50 weight percent moisture was placed in a variable shear batch knife mixer and ground to small (approximately 3 to 7 millimeters in diameter) particles. Heated stock copper chloride-potassium chloride solution in the amount of 159.8 grams was added by pouring evenly over the small particles. Additional mixing was performed to produce a paste of activated clay. Judged by color and texture, the paste was homogeneous.

The activated clay paste was introduced to an extruder which forced the material through a die having openings 6.4 millimeters in diameter to produce extrudates of uniform diameter. The extrudates were dried in batches in ovens at 140° C. for 16 hours or until no weight change was observed. The resulting dried material was placed into containers and calcined in a furnace batchwise at 700° C. for 4 hours.

The calcined material from the furnace was allowed to cool and then ground to produce a first catalyst containing 6.7 percent copper by weight and 5.4 percent potassium by weight and having the particle size distribution shown in Table 1.

TABLE 1

| Size, US Mesh | Particles Retained, Weight Percent |
| --- | --- |
| 70 | 7.3 |
| 100 | 48.5 |
| 120 | 13.7 |
| 140 | 16.5 |
| 170 | 11.5 |
| 200 | 2.4 |

For purposes of comparison, a traditional baseline catalyst having a nearly identical particle size distribution as the first catalyst, was made by spraying an aqueous solution of cupric chloride and potassium chloride on calcined attapulgus clay granules in a rotary mixer. The temperature of both the solution and the granules during spraying was 60° C. The wet granules were dried to less than 2 percent moisture by weight and screened to produce the baseline catalyst containing 6.5 percent copper by weight and 4.9 percent potassium by weight and having the particle size distribution shown in Table 2.

TABLE 2

| Size, US Mesh | Particles Retained, Weight Percent |
| --- | --- |
| 70 | 5.0 |
| 100 | 42.4 |
| 120 | 26.3 |
| 140 | 17.3 |
| 170 | 7.0 |
| 200 | 2.0 |

Ethylene was oxyhydrochlorinated in several runs using the fluidized bed reactor described above. The reactor was charged with from 993 to 1016 grams of the first catalyst and operated at hotspot temperatures of about 300° C. and contact times of about 12 seconds. Ethylene, anhydrous hydrogen chloride, oxygen, and nitrogen were fed to the reactor. Ethylene:hydrogen chloride mole ratios of from 0.583:1 to 0.604:1 were utilized, while oxygen:hydrogen chloride mole ratios varied between 0.253:1 to 0.287:1. Nitrogen:hydrogen chloride mole ratios varied from 0.311:1 to 0.317:1. Hydrogen chloride utilizations were from 97.6 to 99.9 percent. Product purity ranged from 97.0 to 98.9 percent 1,2-dichloroethane, by weight. By-product chloral formation was reduced by 50 to 75 percent compared to use of the traditional baseline catalyst under similar conditions.

EXAMPLE 2

A 2-liter Erlenmeyer flask was charged with 829.3 grams of deionized water. The water was heated to 60° C. after which 263.9 grams of potassium chloride was added. The contents of the flask were stirred until all solids were dissolved to thereby produce a first stock potassium chloride solution.

Four hundred grams of milled raw attapulgite clay containing approximately 50 weight percent moisture was placed in a variable shear batch knife mixer and slightly ground to break up large agglomerates. Technical grade CuO powder in the amount of 25.42 grams was sprinkled evenly over the slightly ground raw clay. The treated clay was further ground to small (approximately 3 to 7 millimeters in diameter) particles. Heated first stock potassium chloride solution in the amount of 117.6 grams was added to the small particles. Additional mixing was performed to produce a paste of activated clay. Judged by color and texture, the paste was homogeneous.

The activated clay paste was introduced to an extruder which forced the material through a die having openings 6.4 millimeters in diameter to produce extrudates of uniform diameter. The extrudates were dried in batches in ovens at 140° C. for 16 hours or until no weight change was observed. The resulting dried material was placed into containers and calcined in a furnace batchwise at 700° C. for 4 hours.

The calcined material from the furnace was allowed to cool and then ground to produce a second catalyst containing 6.9 percent copper by weight and 6.5 percent potassium by weight and having the particle size distribution shown in Table 3.

TABLE 3

| Size, US Mesh | Particles Retained, Weight Percent |
|---|---|
| 70 | 11.8 |
| 100 | 45.7 |
| 120 | 14.4 |
| 140 | 14.3 |
| 170 | 10.8 |
| 200 | 3.0 |

Etylene was oxyhydrochlorinated in several runs using the fluidized bed reactor described above. The reactor was charged with 1006 grams of the second catalyst and operated at hotspot temperatures of about 300° C. and contact times of about 12 seconds. Ethylene, anhydrous hydrogen chloride, oxygen, and nitrogen were fed to the reactor. Ethylene:hydrogen chloride mole ratios of 0.577:1 to 0.604:1 were utilized, while oxygen:hydrogen chloride mole ratios varied from 0.240:1 to 0.287:1 and nitrogen:hydrogen chloride mole ratios varied from 0.308:1 to 0.317:1. Hydrogen chloride utilizations were from 95.3 to 99.7 percent. Product purity ranged from 97.3 to 98.8 percent 1,2-dichloroethane, by weight. By-product chloral formation was reduced by 50 to 59 percent compared to use of the traditional baseline catalyst described in Example 1 under similar conditions.

EXAMPLE 3

A 2-liter Erlenmeyer flask was charged with 1477.8 grams of deionized water. The water was heated to 60° C. after which 287.01 grams of potassium chloride was added. The contents of the flask were stirred until all solids were dissolved to thereby produce a second stock potassium chloride solution.

Four hundred grams of milled raw attapulgite clay containing approximately 50 weight percent moisture was placed in a variable shear batch knife mixer and slightly ground to break up large agglomerates. Technical grade CuO powder in the amount of 25.4 grams was sprinkled evenly over the slightly ground raw clay. The treated clay was further ground to small (approximately 3 to 7 millimeters in diameter) particles. Hot deionized water in the amount of 89.7 grams was added to small particles. Additional mixing was performed to produce a paste. Judged by color and texture, the paste was homogeneous.

The activated clay paste was introduced to an extruder which forced the material through a die having openings 6.4 millimeters in diameter to produce extrudates of uniform diameter. The extrudates were dried in batches in ovens at 140° C. for 113 hours or until no weight change was observed. The resulting dried material was placed into containers and calcined in a furnace batchwise at 700° C. for 4 hours.

The calcined material from the furnace was allowed to cool and then ground to produce an intermediate product having the particle size distribution shown in Table 4.

TABLE 4

| Size, US Mesh | Particles Retainied, grams |
|---|---|
| 70 | 140.24 |
| 100 | 910.19 |
| 120 | 334.31 |
| 140 | 385.25 |
| 170 | 181.94 |
| 200 | 74.06 |

A 20-liter baffled rotary evaporator flask was charge with 2014.9 grams of the intermediate product and affixed to a Büchi® Rotovap evaporator. Rotation of the flask was set at 50 revolutions per minute (rpm) and the flask lowered into a hot water bath ranging in temperature from 72° C. to 92° C. A mechanical vacuum pump was used to evacuate the rotary evaporator to 70 centimeters of mercury vacuum.

The 2-liter Erlenmeyer flask containing the second stock potassium chloride solution at 60° C. was equipped with a magnetic stirring bar and placed on a heated magnetic stir plate. A three-hole stopper was fitted to the top, with one hole plugged, one hole open for a vent, and one hole equipped with a 3.175 millimeter perfluoroalkoxy tubing dip tube down to the bottom of the flask. The other end of the tubing was passed through a stopcock valve sealed by latex tubing, and threaded down the throat of the Rotovap into the flask to terminate above the rotating solids just past the neck of the flask. The tubing was cut in the middle and each end was connected to a Masterflex® tubing pump (Cole-Parmer Instrument Co., Vernon Hills, Ill., USA) equipped with C-Flex® elastomeric tubing (part number 6424-14) (Cole-Parmer Instrument Co.) set in a Masterflex® 7014-52 pump head fitted to a variable speed motor with a range of from 6 to 600 rpm. The pump was used to pump hot second stock potassium chloride solution from the 2-liter Erlenmeyer flask into the Rotovap flask where the solution was added to the rotating solids in drop-wise fashion while the solids tumbled at 50 rpm. Pump speed was varied to obtain a solution feed rate of 1.2 to 1.7 grams/minute. Processing continued until all of the second stock potassium chloride solution was added to the solids present in the Rotovap. When addition of the solution had been completed, the solids were tumbled at bath temperatures of from 72° C. to 90° C. for one hour under a 70 centimeters of mercury vacuum. Heating was discontinued, the vacuum was released, and the solids were allowed to cool overnight to produce a third catalyst weighing 2130.44 grams and containing 7.1 percent copper by weight and 6.4 percent potassium by weight. The third catalyst had the particle size distribution shown in Table 5.

TABLE 5

| Size, US Mesh | Particles Retained, Weight Percent |
|---|---|
| 70 | 8.1 |
| 100 | 42.6 |
| 120 | 22.3 |

TABLE 5-continued

| Size, US Mesh | Particles Retained, Weight Percent |
| --- | --- |
| 140 | 10.7 |
| 170 | 7.8 |
| 200 | 5.2 |
| PAN | 2.9 |

Ethylene was oxyhydrochlorinated in several runs using the fluidized bed reactor described above. The reactor was charged with 1094.6 grams of the third catalyst and operated at hotspot temperatures of about 300° C. and contact times of about 13 seconds. Ethylene, anhydrous hydrogen chloride, oxygen, and nitrogen were fed to the reactor. Ethylene:hydrogen chloride mole ratios of 0.577:1 to 0.604:1 were utilized, while oxygen:hydrogen chloride mole ratios varied from 0.240:1 to 0.287:1 and nitrogen:hydrogen chloride mole ratios varied from 0.308:1 to 0.317:1. Hydrogen chloride utilizations were from 98.1 to 99.9 percent. Product purity ranged from 97.4 to 98.8 percent 1,2-dichloroethane, by weight. By-product chloral formation was reduced by 40 to 61 percent compared to use of the traditional baseline catalyst described in Example 1 under similar conditions.

Although the present invention has been described with reference to specific details of certain embodiments thereof, it is not intended that such details should be regarded as limitations upon the scope of the invention except insofar as they are included in the accompanying claims.

What is claimed is:

1. A process for producing oxychlorination catalyst comprising:
    (a) mixing together wet support material and copper chloride or precursor thereof to form a paste, wherein the wet support material is wet clay, wet silica, wet silica gel, wet alumina, wet diatomaceous earth, or a mixture of two or more thereof;
    (b) removing water from the paste to produce a substantially dry mixture; and
    (c) calcining the substantially dry mixture at elevated temperatures of at least 600° C. to produce a calcined mixture;
wherein:
    (d) alkali metal chloride or a precursor thereof is mixed with the wet support material and copper chloride or precursor thereof, to form the paste; or
    (e) an aqueous solution of alkali metal chloride or precursor thereof is applied to the paste, the substantially dry mixture, the calcined mixture, or two or more thereof, and the water of the aqueous solution is substantially removed.

2. The process of claim 1 wherein alkali metal chloride or a precursor thereof is mixed with the wet support material and copper chloride or precursor thereof, to form the paste.

3. The process of claim 2 wherein the wet support material is wet clay.

4. The process of claim 3 wherein the wet clay is wet attapulgus clay.

5. The process of claim 4 wherein wet attapulgus clay, a precursor of copper chloride, and alkali metal chloride are mixed together to form the paste.

6. A process for producing oxychlorination catalyst comprising:
    (a) mixing together wet attapulgus clay, a precursor of copper chloride and alkali metal chloride to form a paste;
    (b) removing water from the paste to produce a substantially dry mixture; and
    (c) calcining the substantially dry mixture at elevated temperatures of at least 600° C. to produce a calcined mixture;
        wherein the precursor of copper chloride is cupric oxide or metallic copper, and the alkali metal chloride is potassium chloride.

7. The process of claim 4 wherein wet attapulgus clay, copper chloride, and alkali metal chloride are mixed together to form the paste.

8. The process of claim 7 wherein the copper chloride is cupric chloride and the alkali metal chloride is potassium chloride.

9. The process of claim 1 wherein an aqueous solution of alkali metal chloride or precursor thereof is sprayed onto the calcined mixture and the water of the aqueous solution is substantially removed.

10. The process of claim 9 wherein the wet support material is wet clay.

11. The process of claim 10 wherein the wet clay is wet attapulgus clay.

12. The process of claim 1 wherein the paste is extruded to form extrudates.

13. The process of claim 1 wherein water is removed from the paste at temperatures in the range of from 80° C. to 200° C. to produce the substantially dry mixture.

14. The process of claim 1 wherein the substantially dry mixture is calcined at temperatures in the range of from 600° C. to 1000° C. to produce the calcined mixture.

15. The process of claim 1 wherein the calcined mixture is ground to form particles.

16. The process of claim 15 wherein the particles are classified according to particle size.

17. Oxychlorination catalyst produced by the process of claim 1.

18. Oxychlorination catalyst produced by the process of claim 2.

19. Oxychlorination catalyst produced by the process of claim 3.

20. Oxychlorination catalyst produced by the process of claim 4.

21. Oxychlorination catalyst produced by the process of claim 5.

22. Oxychlorination catalyst produced by the process of claim 6.

23. Oxychlorination catalyst produced by the process of claim 7.

24. Oxychlorination catalyst produced by the process of claim 8.

25. Oxychlorination catalyst produced by the process of claim 9.

26. Oxychlorination catalyst produced by the process of claim 10.

27. Oxychlorination catalyst produced by the process of claim 11.

28. Oxychlorination catalyst produced by the process of claim 12.

29. Oxychlorination catalyst produced by the process of claim 13.

30. Oxychlorination catalyst produced by the process of claim 14.

31. Oxychlorination catalyst produced by the process of claim 15.

32. Oxychlorination catalyst produced by the process of claim 16.

* * * * *